United States Patent

Janik et al.

Patent Number: 5,900,152
Date of Patent: May 4, 1999

[54] APPARATUS TO REDUCE INHOMOGENEITIES IN OPTICAL FLOW CELLS

[75] Inventors: Gary R. Janik, Palo Alto; Douglas W. Shepard; Steven T. Monser, both of Santa Barbara, all of Calif.

[73] Assignee: Wyatt Technology Corporation, Santa Barbara, Calif.

[21] Appl. No.: 08/854,442

[22] Filed: May 12, 1997

Related U.S. Application Data

[62] Division of application No. 08/632,035, Apr. 12, 1996, Pat. No. 5,676,830.

[51] Int. Cl.$^6$ .................................................. B01D 15/08
[52] U.S. Cl. ..................... 210/656; 210/198.2; 73/61.58; 356/128; 356/246; 422/70
[58] Field of Search ..................... 210/656, 659, 210/198.2; 73/61.52, 61.58; 356/128, 246, 318; 422/70; 436/161

[56] References Cited

U.S. PATENT DOCUMENTS

| | | | |
|---|---|---|---|
| 3,975,104 | 8/1976 | Munk | 356/246 |
| 4,006,990 | 2/1977 | Munk | 356/246 |
| 4,455,089 | 6/1984 | Yeung | 356/246 |
| 4,500,432 | 2/1985 | Poole | 210/198.2 |
| 4,548,498 | 10/1985 | Folestad | 356/318 |
| 4,675,300 | 6/1987 | Zare | 356/344 |
| 4,900,435 | 2/1990 | Anderson | 210/198.2 |
| 4,900,446 | 2/1990 | Anderson | 210/198.2 |
| 4,952,055 | 8/1990 | Wyatt | 356/128 |
| 5,057,216 | 10/1991 | Chervet | 210/198.2 |
| 5,139,661 | 8/1992 | Kolbert | 210/198.2 |

OTHER PUBLICATIONS

Yau, Modern Size Exclusion Liquid Chromatography, John Wiley & Sons, New York 1979, pp. 126 & 146–151.
Dolan, "Extra Column Effects", LC–GC, vol. 10, No. 1, 1992, pp. 20–25.
Martin, "Problems in Equipment Design," Journal of Chromatography, vol. 108, 1975, pp. 229–241.

Primary Examiner—Ernest G. Therkorn
Attorney, Agent, or Firm—Philip J. Wyatt

[57] ABSTRACT

A capillary tube used to transfer a liquid sample into a detection cell following separation by a chromatographic system is modified by plugging or otherwise severely restricting its flow. Near its plugged end, said tube is drilled to provide a plurality of holes or ports perpendicular thereto and penetrating to the central flowing core of said tube so as to direct outflow from the tube perpendicularly therefrom. The outer diameter of this somodified capillary tube is selected to be of a size comparable to, though smaller than, the detection cell diameter into which it transfers the flowing sample. In this manner, fluid transferred into a detection cell by said modified capillary tube will be split into a plurality of smaller streams flowing outwardly therefrom and striking the adjacent detector cell walls almost immediately. Because of the close proximity of the emerging split streams to the walls of the detection cell, the eddies produced thereby will be very small and the contents of the detection cell will be homogenized rapidly.

2 Claims, 4 Drawing Sheets

APPARATUS TO REDUCE INHOMOGENEITIES IN OPTICAL FLOW CELLS

This application is a division of application Ser. No. 08/632,035, filed Apr. 12, 1996, now U.S. Pat. No. 5,676,830.

DEFINITIONS

Sample: Material such as a polymer or biopolymer which is to be separated and analyzed.

Solvent: The liquid or gas in which the sample is dissolved and carried through the chromatographic system.

Chromatographic system: Apparatus used to separate and analyze samples which generally includes fractionation/separation means such as columns.

BACKGROUND

Measurement of the molecular weight distribution of polymers is an important part of polymer characterization and is of great interest to those studying, developing, or producing synthetic or natural polymers. One of the most accurate methods for measuring the molecular weight distribution of a sample is to use size exclusion chromatography to separate the polymers by size in a flowing system and then to use a light scattering detector to measure the molecular weight of each eluting fraction. The separation by size becomes a separation in time as the largest molecules flow out of the end of the chromatographic system first, followed by slightly smaller molecules, with the smallest molecules coming last. The profile of the polymer concentration versus time at a point along the flow generally consists of one or more smooth peaks. If the original sample consists of a wide continuous range of molecular weights, there will be a single very broad peak and the sample is said to be polydisperse. If the sample was very homogeneous and only had a very small range of molecular weights, the peak is narrow and the sample is described as being monodisperse. An important concept is that of a slice, defined as an instantaneous short section of flow along which the polymer is homogeneous and the concentration constant. A peak is composed of many slices arranged end to end.

As the molecules in their solvent flow out of the chromatographic system they may flow next into light scattering detection instrumentation which produces electrical signals proportional to the light scattered in various directions by the scattering sample. In this way, the molecular weight can be determined as a function of time and then related back to the distribution of molecular weight in the polymer sample. In order to determine the molecular weight, however, an additional measurement is necessary, namely the sample concentration as a function of time.

The most common way to measure the concentration as a function of time is to use a refractive index detector to measure the change in refractive index which is proportional to the polymer concentration. In practice, this is always done in a second instrument downstream from the light scattering instrument. The information that is necessary to determine molecular weight is the light scattering,intensity extrapolated to zero scattering angle and the concentration for each slice. In particular, it is necessary to match each slice of the extrapolated light scattering intensity with the corresponding slice of the concentration signal.

The light scattering and concentration signals are produced by two different instruments separated by a short length of tubing. This means there will be a time delay between corresponding slices which must be determined. In addition, the connecting tubing as well as the flow cells of the two instruments create some mixing of the flow which tends to degrade the polymer separation/fractionation performed by the chromatographic system. In other words, it broadens the peak. This effect is called interdetector band broadening, in contrast to traditional column band broadening, and underscores the fact that the concept of a slice is not completely valid. A short section of flow does not remain unchanged as it travels through the system, but mixes somewhat with other slices during its passage from one detector to the next. It is not possible, therefore, to measure both the light scattering and concentration of the same slice since the same slice cannot exist at both locations. The contamination of a slice with sample fractions from other slices as it travels from one detector to another will create errors in the measurement of the molecular weight distribution. The effect of interdetector band broadening must be kept small to minimize measurement errors for samples of small polydispersity. When samples span a broad, continuous range of molecular weights, such interdetector band broadening effects are rarely noticed and usually are of little importance.

Interdetector band broadening has deleterious effects in all chromatography systems containing more than a single detector and efforts to reduce it have a substantial history. The broadening due to flow in long tubes has been well studied and it is known that the effect is greatly reduced by using very small diameter tubes. For this reason, standard fluid chromatography tubing is now made with an inside diameter of 0.25 mm which is the smallest practical size. The broadening due to optical flow cells is highly dependent on the flow pattern inside the cell and hence highly dependent on the design. In general, the smaller the cell volume, the smaller the broadening. In cells designed for refractive index detectors, as well as in other optical instruments such as light scattering detectors, there are at least two factors which limit how small the cell volume can be. One is the optical path length of the light beam through the cell. Usually the sensitivity of the detector will be proportional to the optical path length so it cannot be made very small. The other factor limiting the miniaturization of the flow cell is the optical beam diameter. The optical beam, especially if not generated by a laser, often cannot be made smaller than a certain dimension. These two minimum dimensions define a minimum cross section. If the sample flow is perpendicular to the optical beam, as is often the case, then the volume will be determined by the product of the minimum cross section and the length along the flow. This length will in general be limited from below by some other practical consideration.

Even for a fixed volume, the broadening depends on the details of the structural geometry and how it affects the flow pattern. The region of introduction of the flow into a detection cell requires particular attention. Since the flow will generally be introduced from a very small diameter tube, the cross section of the flow will be initially very much smaller than the minimum cross section of the cell as determined by the optical path length and beam diameter. This will generally cause the flow to become non-laminar and create eddies. These eddies can extend the full length of the flow cell. The flow reaches the far end of the cell, turns around, and flows back to the point of entry where it repeats the process. This rotational motion, or eddy, mixes flow between slices separated by multiples of the full volume of the flow cell and can cause serious interdetector band broadening.

In most discussions of interdetector band broadening, the phenomena are considered to be a random statistical process of solute mixing as discussed, for example, by W. W. Yau in his book Modern Size Exclusion Liquid Chromatography published by John Wiley & Sons in 1979. A detailed discussion by J. C. Dolan in his article published in volume 10 of LCGC, pages 20 through 25, in 1992 discusses many types of interdetector band broadening, but only in this same statistical sense. Thus the actual details of the flow eddies that occur whenever the diameters of the successive components change are neither discussed nor noted. All such band broadenings are treated as successive Gaussian broadenings of different weightings to yield an estimate of the contributions of each to the final total broadening. A particularly innovative element of our invention relates to our detailed experimental studies of the various eddy patterns that occur during the transition of flow from a very small diameter stream to one of much larger diameter such as occur within the optical detection cells. By studying these eddies, their formation and destruction, we have been able to address these interdetector band broadening effects and have developed methods and apparatus for their reduction, as shall be presented herein. In contrast to our approach, the traditional methods as described, for example, by Dolan are comprised of procedures to minimize such effects by using ". . . small injection volumes . . ., short runs of small internal diameter tubing that connect the column to the rest of the system, and a method-appropriate detector cell volume . . ." Our invention is directed to modify the detector cell volume. Martin, et al. discuss band broadening in the detector in their 1975 article in the Journal of Chromatography in volume 108 beginning on page 229.

There have been many inventions developed over the years concerned with the homogenization of two or more fluids that are to be mixed. Our invention is quite distinct from these earlier procedures as there is only a single fluid present in the detection cell but, because of its changing composition, the composition within the cell is correspondingly changing and often inhomogeneous. Although the flow in a detection cell is continuous with the flow in the inlet capillary bringing the sample to the cell, the spatial and temporal concentration distribution within the cell does not generally mimic the concentration distribution in the transferring capillary. The sharp temporal concentration changes within the capillary that transfers the separated sample into the detection cell results in a chaotic inhomogeneity of concentration within the detection cell itself, as has been discussed above. A very small diameter flow suddenly increases its cross section by many fold as it moves from the tube into the detection cell and undergoes a chaotic disruption within the whole cell volume. The basic objective and achievement of this invention is to confine this flow disruption to the smallest possible volume in the shortest possible time and not allow the entire cell to act as a large mixing chamber by eliminating spatially large scale eddies within the detection cell.

BRIEF DESCRIPTION OF THE INVENTION

The invention described here is a design modification to an optical detection cell where the flow is introduced into the cell in such a way as to generate much smaller eddies than in a conventional design in order to reduce greatly the interdetector band broadening occurring therein. The basic feature of the modified design of the present invention is a new means for introducing flow into the cell incorporating several small streams directed at right angles to the normal flow axis of the cell. Each flow stream originates close to the transverse cell boundary which it strikes causing it to change direction quickly. The key point is that the transverse dimension of the flow cell is much smaller than the longitudinal dimension and the eddy is correspondingly much smaller. The eddies mix slices which are much more closely spaced than with the ordinary design and the interdetector band broadening is much reduced.

DETAILED DESCRIPTION OF THE INVENTION

Figure 1:
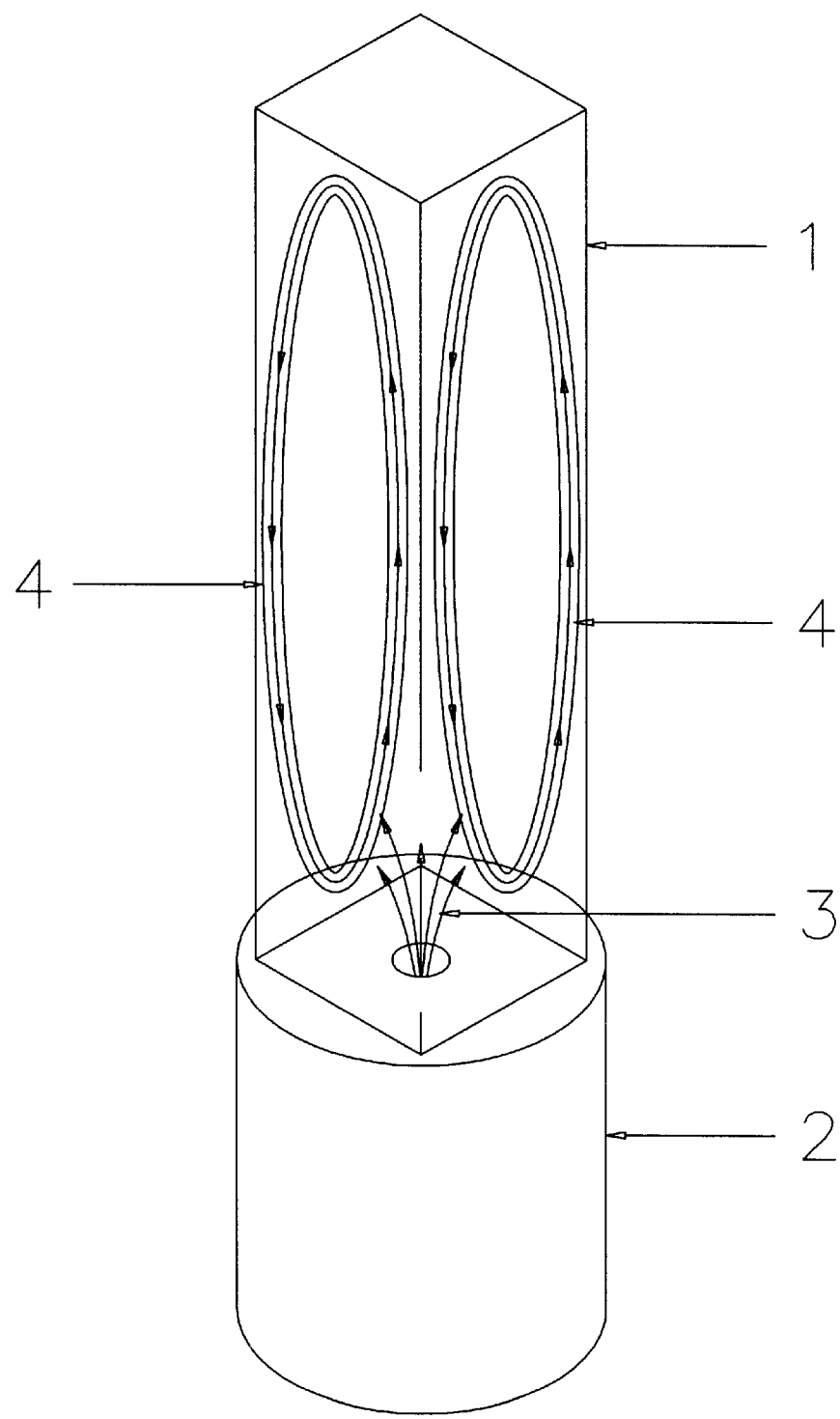
FIG. 1 is a drawing of a conventional longitudinal flow optical cell showing a small injection orifice and the correspondingly large eddies.

FIG. 1 shows a cutaway view of a conventional cell design such as implemented in the Optilab interferometric refractometer manufactured by Wyatt Technology Corporation and often used to monitor sample concentration of a chromatographically separated sample. The internal volume of the cell 1 has the shape of a square prism. The transverse, square dimension is 1 mm and the longitudinal dimension is 7 mm. The inflow 3 is along the longitudinal direction and is introduced by means of a tube 2 with, say, a 0.25 mm internal diameter and 1.58 mm outside diameter and joined to the base of the optical cell. The flow pattern is shown as arrows with eddies indicated by 4. The length of the eddies, is a large fraction of the cell length, causing mixing of widely separated slices.

Figure 2:
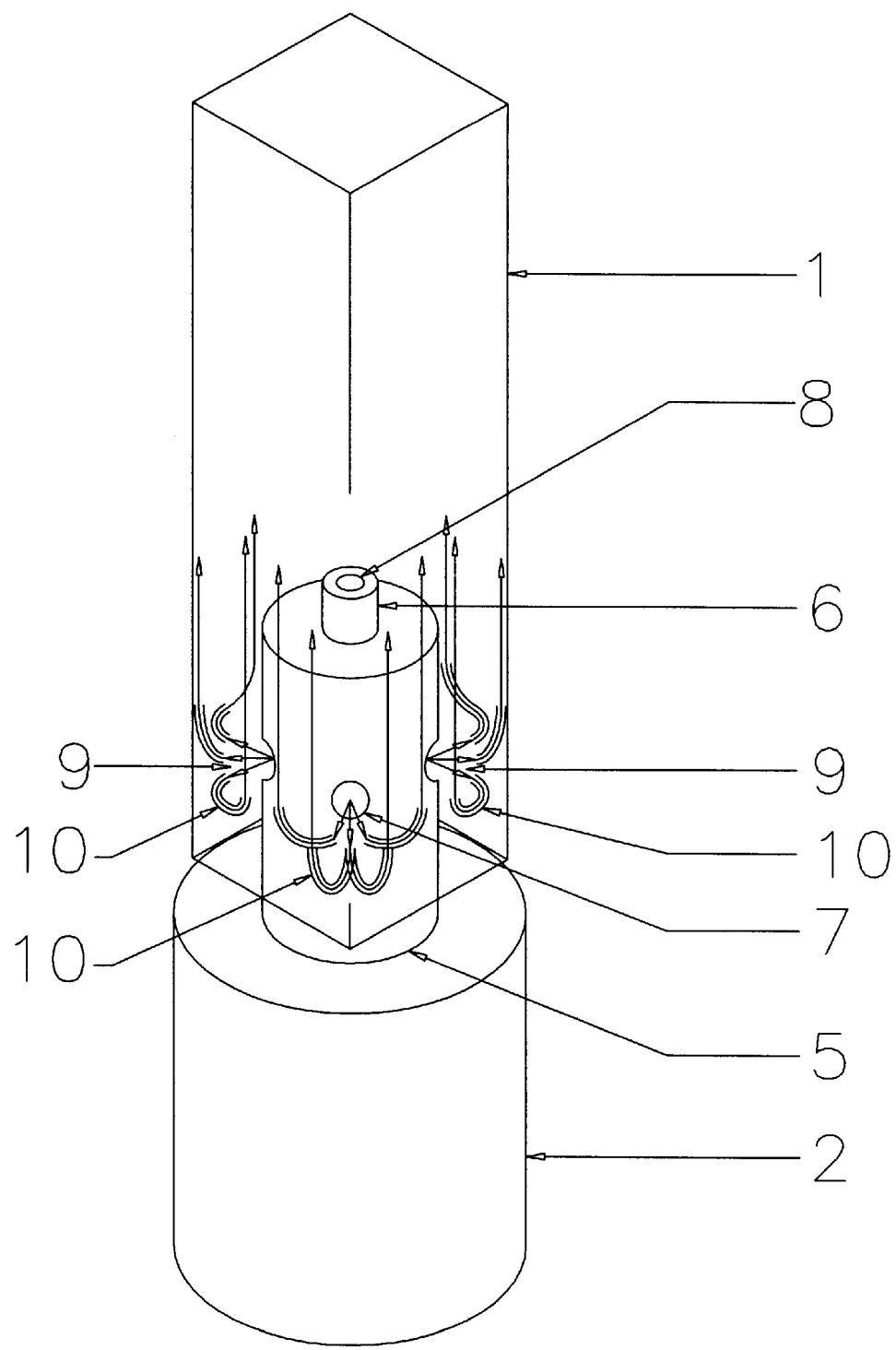
FIG. 2 is a drawing of a new design of longitudinal flow optical cell with the flow introduced by means of several small streams flowing in the transverse direction as they leave the sample introduction tube, creating thereby smaller, more homogeneous eddies.
Figure 3:
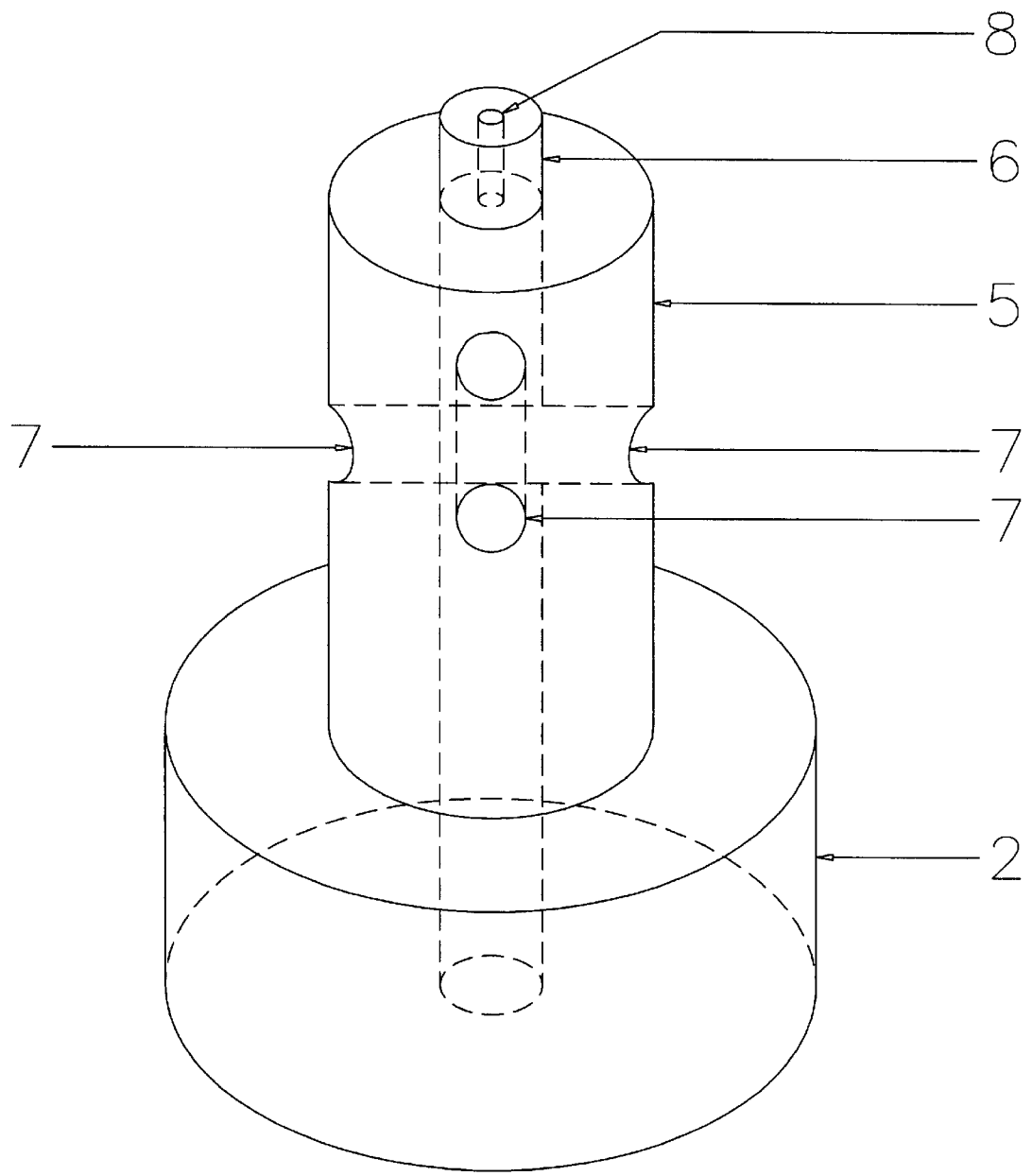
FIG. 3 is an expanded view of the sample introduction tube for the new flow cell with four transverse holes intersecting the sample flow within said tube.

FIG. 2 shows a similar cutaway view of the new cell design. The cell shape and dimensions are the same as in FIG. 1, but the flow is now introduced by a tube 2 that has been modified at 5 as shown in more detail in FIG. 3. Modified tube section 5, in its preferred embodiment, would be constructed from traditional narrow bore tubing 2 by turning down a small section of the outer diameter of 1.58 mm to a smaller 0.79 mm diameter as indicated in FIG. 3. The tube has a plug 6 inserted at the end and has multiple flow orifices 7 oriented in multiple locations in a plane transverse thereto. Instead of a plug, the end of the tube could be crimped or crushed closed. The plug 6 stops the flow in the longitudinal direction and the orifices redirect and split it into several transverse streams 9. The plug itself may have a small orifice 8 at its terminal end permitting a small longitudinal flow component. The transverse streams hit the cell wall, turn around and return to either the originating orifice or another one and form smaller eddies 10. The size of the eddy is determined by, the distance from the orifice to the cell wall. Typically, the transverse dimension of the cell is 1 mm and the diameter of the cylindrical surface of 5 in which the orifices lie is 0.79 mm, leaving only 0.11 mm between the orifice and the cell wall. Thus the cylindrical surface diameter is a major fraction of the transverse diameter of the cell itself. For certain types of cell geometries, the transverse streams may have special orientations. For example, if the flow cell is of square cross section, it may be desirable to orient some of the transverse streams toward the corners of the cell. Alternatively, it may be preferable to orient the streams towards the closest boundaries, i. e. the walls themselves.

Designing the orifice surface 5 diameter to be a large fraction of the cell transverse dimension leaves very little room for eddies and greatly reduces the band broadening. Dividing up the original flow into several smaller streams creates many smaller eddies instead of a smaller number of larger ones, also contributing to a smaller broadening. Although the preferred embodiment of this invention provides for the transverse streams to exit the sample in-flow tube in close proximity to the walls of the optical cell, say within 5% to 50% of the cell radius, even without being close, these streams still will result in significant reduction to the interdetector band broadening because their initial transverse flow helps remove and mix fluids that would have remained in stagnant regions near the entrance of the optical cell.

Figure 4:
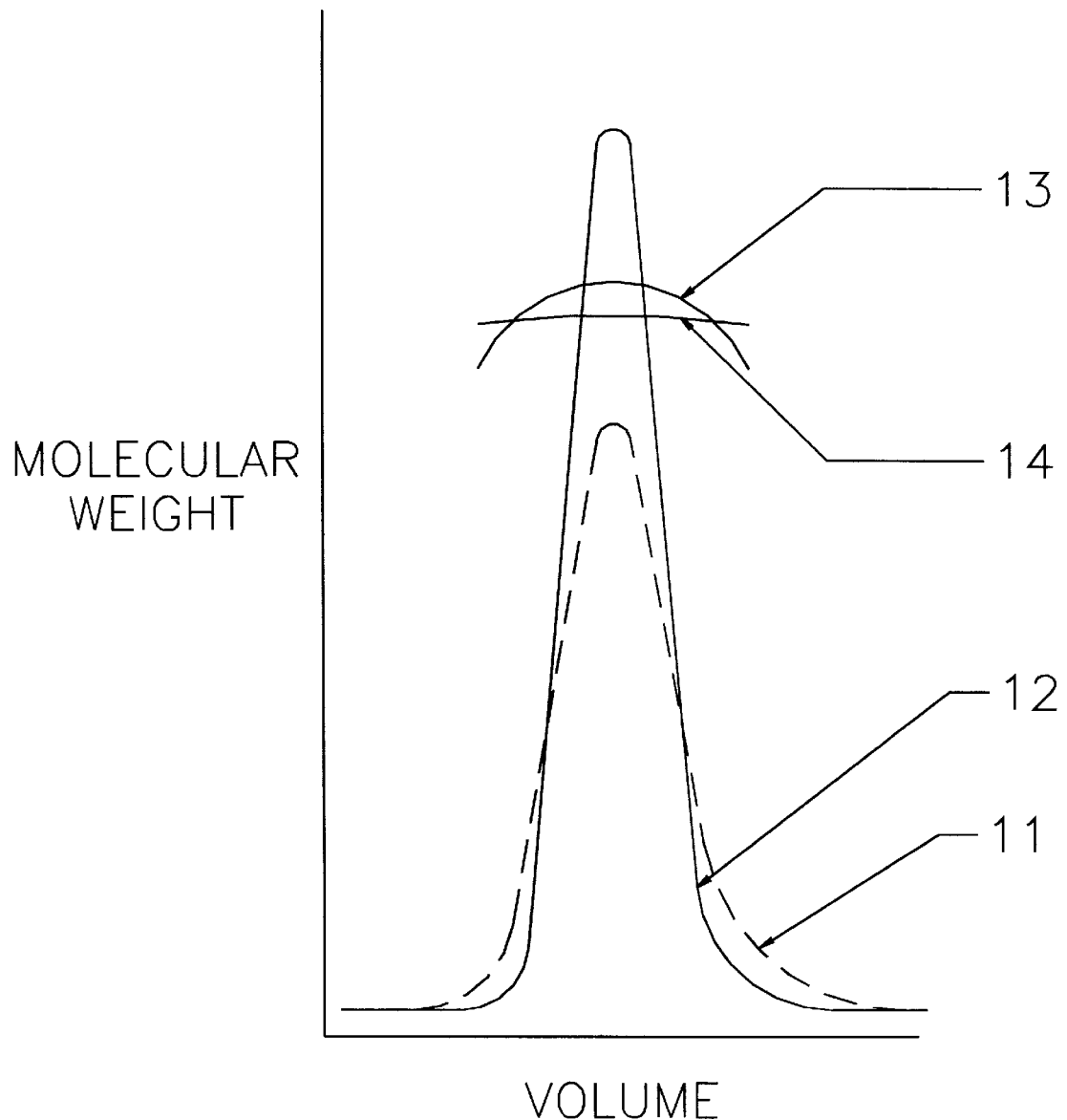
FIG. 4 is a plot of the molecular weight distribution of a monodisperse polystyrene polymer as measured with both a conventional sample introduction tube and the new design disclosed.

Molecular weight distribution measurements can be performed with two different cells to compare the band broadening effects of each one. A monodisperse polymer sample has been measured which yields an almost flat molecular weight response with elution in the absence of interdetector broadening. Polymer samples with such a narrow molecular weight range are commercially available as so-called calibration standards. We have used a narrow polystyrene standard with a molecular weight of about 200,000 gms/mole to compare the performance of the old and new designs. Theresults of two such measurements are illustrated in FIG. 4. The signal 11 from the concentration detector is plotted versus eluted flow volume and shows a characteristic peak shape. The corresponding light scattering signal at 90° is shown at 12. If there were no interdetector band broadening, the molecular weight of the sample at the central region would be proportional to the ratio of the light scattering signal to the concentration detector signal. With interdetector broadening due to the old cell design, the molecular weight variation across the peak as indicated as 13 is obtained. This does not correspond, of course, to the near absence of molecular weight variation across the peak that is expected for such a narrow standard. With the new cell design of FIG. 3, the molecular weight variation across the peak is indicated by the trace 14. As has been discussed above, a perfect measurement system would yield an almost constant molecular weight value across the peak, i. e. a nearly flat horizontal line. It is easy to see that the new cell design produces much closer agreement with this ideal measurement than does the conventional cell. The interdetector broadening error shows up as a spurious, grimace-like variation of molecular weight across the peak. Our measurements show an improvement of about a factor of 8 less variation in molecular weight when using the new cell.

In summary, our invention, whose exemplar has been discussed previously, is based on a modified flow tube, through which a fluid or gas sample is transferred into an optical detection cell, with the following features:

a) The sample is transported into the optical cell via a tube whose outer diameter is a major fraction of the diameter of the optical cell;

b) The tube has a plurality of holes transverse to it and penetrating to the transported sample flowing through its inner core;

c) There is a plug at the end of the tube restricting the sample flow and forcing it thereby to split and flow outwardly via a set of secondary streams, each of which flows through one of the transverse holes;

d) Each secondary stream flowing out of a transverse hole strikes a nearby adjacent cell wall, creating thereby a set of much smaller eddies than will occur in a standard flow cell whose diameter is much greater than the flow stream diameter entering the cell.

As will be evident to those skilled in the arts of chromatography, there are many obvious variations of the apparatus we have invented and described that do not depart from the fundamental elements that we have listed for its practice; all such variations are but obvious implementations of our invention described hereinbefore and are included by reference to our claims, which follow.

We claim:

1. A method for minimizing interdetector band broadening arising from inhomogeneous flow within an optical detection cell by splitting the sample flow entering said optical detection cell into a plurality of streams directed transverse to said inflow direction and directed towards the side walls of said optical cell, producing thereby a homogeneous mixing within said cell.

2. The method of claim 1 where said optical detection cell is an element of a refractive index detector.

* * * * *